US011622895B2

United States Patent
Anousis et al.

(10) Patent No.: US 11,622,895 B2
(45) Date of Patent: Apr. 11, 2023

(54) SANITARY PAD SYSTEM WITH TWO PADS HAVING OFFSET ADHESIVE TABS FOR ATTACHMENT TO AN UNDERGARMENT

(71) Applicants: Angelica M. Anousis, Quincy, MA (US); Maria A. Theodore, Quincy, MA (US)

(72) Inventors: Angelica M. Anousis, Quincy, MA (US); Maria A. Theodore, Quincy, MA (US)

( * ) Notice: Subject to any disclaimer, the term of this patent is extended or adjusted under 35 U.S.C. 154(b) by 546 days.

(21) Appl. No.: 16/824,369

(22) Filed: Mar. 19, 2020

(65) Prior Publication Data

US 2021/0121336 A1    Apr. 29, 2021

Related U.S. Application Data

(60) Provisional application No. 62/927,295, filed on Oct. 29, 2019.

(51) Int. Cl.
| | |
|---|---|
| *A61F 13/56* | (2006.01) |
| *A61F 13/505* | (2006.01) |
| *A61F 13/514* | (2006.01) |
| *A61F 13/58* | (2006.01) |

(52) U.S. Cl.
CPC ........ *A61F 13/5616* (2013.01); *A61F 13/505* (2013.01); *A61F 13/51401* (2013.01); *A61F 13/5611* (2013.01); *A61F 13/581* (2013.01); *A61F 2013/51411* (2013.01); *A61F 2013/586* (2013.01)

(58) Field of Classification Search
CPC ...... A61F 13/47; A61F 13/472; A61F 13/474; A61F 13/476; A61F 13/505; A61F 13/5605; A61F 13/5611; A61F 13/5616; A61F 2013/5055; A61F 2013/586
See application file for complete search history.

(56) References Cited

U.S. PATENT DOCUMENTS

| | | | |
|---|---|---|---|
| 5,575,786 A | 11/1996 | Osborn, III | |
| 5,599,339 A * | 2/1997 | Horney | A61F 13/474 604/389 |
| 5,704,932 A | 1/1998 | Hibbard | |
| 5,720,738 A | 2/1998 | Clark | |
| 5,785,698 A | 7/1998 | Van Iten | |
| 5,820,616 A * | 10/1998 | Horney | A61F 13/474 604/385.04 |
| 5,910,137 A | 6/1999 | Clark et al. | |
| 6,013,064 A * | 1/2000 | Yamada | A61F 13/474 604/385.01 |
| 6,176,850 B1 | 1/2001 | Rosenfeld et al. | |
| 6,443,932 B1 | 9/2002 | Maggiulli | |

(Continued)

FOREIGN PATENT DOCUMENTS

EP    0930053 B1    4/2004

*Primary Examiner* — Catharine L Anderson
(74) *Attorney, Agent, or Firm* — Warren D. Schickli; Stites & Harbison PLLC (57) ABSTRACT

A sanitary pad system includes a first pad and a second pad. The first pad has a first set of fastening tabs and the second pad has a second set of fastening tabs. The two sets of fastening tabs are offset so that, when the two pads are stacked in overlapping relationship on an undergarment, both pads are directly attached to the undergarment with the associated fastening tabs.

18 Claims, 6 Drawing Sheets

(56) References Cited

U.S. PATENT DOCUMENTS

| | | | |
|---|---|---|---|
| 6,730,067 B1* | 5/2004 | Nukina | A61F 13/474 604/385.01 |
| 7,160,278 B2 | 1/2007 | Mizutani et al. | |
| 8,042,194 B2 | 10/2011 | Connor | |
| 8,062,275 B2 | 11/2011 | Plentovich et al. | |
| 8,986,273 B2 | 3/2015 | Mercer et al. | |
| 9,125,772 B2 | 9/2015 | Eilers et al. | |
| 9,173,783 B1 | 11/2015 | Terian et al. | |
| 9,980,856 B2 | 5/2018 | Wilson | |
| 2001/0027304 A1 | 10/2001 | Mayer | |
| 2002/0026167 A1 | 2/2002 | Pompa | |
| 2005/0283131 A1 | 12/2005 | Zander et al. | |
| 2018/0325750 A1 | 11/2018 | Vohwinkel et al. | |
| 2020/0222253 A1* | 7/2020 | Roszkowiak | A61F 13/539 |

* cited by examiner

SANITARY PAD SYSTEM WITH TWO PADS HAVING OFFSET ADHESIVE TABS FOR ATTACHMENT TO AN UNDERGARMENT

This application claims the benefit of U.S. Patent Application Ser. No. 62/927,295 filed on 29 Oct. 2019, the full disclosure of which is incorporated herein by reference.

TECHNICAL FIELD

This document relates generally to a new and improved feminine hygiene product in the form of a sanitary pad system adapted for absorbing blood excreted from the vagina of the wearer during the menstrual cycle as well as for other conditions.

BACKGROUND

Many different sanitary pads and sanitary pad systems have been developed over time and some of those are currently being commercially marketed. Despite many advances in design over the years, further improvements are still possible, particularly, as related to ease of use and effectiveness in operation.

The pads and the sanitary pad system disclosed in this document addresses these and other concerns and represents a significant advance in the art.

SUMMARY

In accordance with the purposes and benefits described herein, a new and improved sanitary pad system is provided. That sanitary pad system comprises (a) a first pad having a first set of fastening tabs and (b) a second pad having a second set of fastening tabs. The second set of fastening tabs is offset from the first set of fastening tabs when the second pad is overlying the first pad. As a consequence of this structural configuration, the first pad and the second pad may both be directly connected to an undergarment of a wearer when the pads are stacked to provide long term absorbent protection for the user. The first pad and the second pad may both include an absorbent material layer, adapted to absorb body exudates, and a liquid impervious backing layer impervious to those exudates.

In one or more of the many possible embodiments of the sanitary pad system, the first set of fastening tabs includes a first fastening tab projecting from a first edge of the first pad and a second fastening tab projecting from a second edge of the first pad. That first fastening tab may be offset from the second fastening tab.

In one or more of the many possible embodiments of the sanitary pad system, the second set of fastening tabs includes a third fastening tab projecting from a first edge of the second pad and a fourth fastening tab projecting from a second edge of the second pad. That third fastening tab may be offset from the fourth fastening tab.

In one or more of the many possible embodiments of the sanitary pad system, the first fastening tab, the second fastening tab, the third fastening tab and the fourth fastening tab may all be semi-circular in shape. Further, the first fastening tab, the second fastening tab, the third fastening tab and the fourth fastening tab may include an adhesive on one face thereof to adhere to the undergarment. In addition, the first fastening tab, the second fastening tab, the third fastening tab and the fourth fastening tab may each include a removable release paper that protects the adhesive prior to use.

In one or more of the many possible embodiments of the sanitary pad system the first and second fastening tabs are semi-circular in shape while the third and fourth fastening tabs are semi-annular in shape. A first receiver, in the form of a closed opening, is defined between the third fastening tab and the first edge of the second pad and a second receiver, also in the form of a closed opening, between the fourth fastening tab and the second edge of the second pad. When the first pad and the second pad are connected to the undergarment in a stacked or overlapping configuration, the first tab engages the undergarment at the first receiver and the second fastening tab engages the undergarment at the second receiver.

The first fastening tab, the second fastening tab, the third fastening tab and the fourth fastening tab of this alternative embodiment may include an adhesive on one face thereof to adhere to the undergarment. In addition, the first fastening tab, the second fastening tab, the third fastening tab and the fourth fastening tab may each include a removable release paper that protects the adhesive prior to use.

In accordance with yet another aspect, a new and improved feminine hygiene method is provided. That method comprises the steps of: (a) connecting a first pad directly to an undergarment of the wearer and (b) connecting a second pad directly to the undergarment of the wearer overlying the first pad.

In one or more embodiments of the method, that method further includes the step of removing the second pad when the second pad has reached the end of its useful life while maintaining the first pad in position connected to the undergarment. Still further, the method may include using a first set of fastening tabs to connect the first pad to the undergarment and using a second set of fastening tabs to connect the second pad to the undergarment wherein the second set of fastening tabs is offset from the first set of fastening tabs.

In the following description, there are shown and described several preferred embodiments of the sanitary pad system and the related feminine hygiene method. As it should be realized, the sanitary pad system and the feminine hygiene method are capable of other, different embodiments and its several details are capable of modification in various, obvious aspects all without departing from the sanitary pad system and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the sanitary pad system and together with the description serve to explain certain principles thereof.

FIG. 1A is a detailed perspective view of a first pad of the first embodiment of the sanitary pad system.

FIG. 1B is a detailed perspective view of a second pad of the first embodiment of the sanitary pad system.

FIGS. 1C-1E are respective detailed side elevational, top plan and bottom plan views illustrating the first embodiment of the sanitary pad system secured in place on an undergarment with the second pad overlying or overlapping the first pad.

FIG. 1F is a cross sectional view taken through the pads stacked on the undergarment.

FIG. 2A is a detailed perspective view of a first pad of the second embodiment of the sanitary pad system.

FIG. 2B is a detailed perspective view of a second pad of the second embodiment of the sanitary pad system.

FIGS. 2C-2E are respective detailed side elevational, top plan and bottom plan views illustrating the second embodiment of the sanitary pad system secured in place on an undergarment with the second pad overlying or overlapping the first pad.

DETAILED DESCRIPTION

This document relates to a sanitary pad system incorporating two or more independent absorbent pads that may be stacked on an undergarment to absorb body exudates such as menses, urine and fecal matter. Advantageously, the pads are secured in position on the undergarment by offset tabs that do not overlap. As a result, each pad is directly secured or connected to the undergarment independent of the other.

This unique configuration of tabs allows one to easily remove and dispose of the top pad at any desired time in a most convenient manner without removing the underlying pad or in any way adversely interfering with the connection of the underlying pad to the undergarment. In other words, the tabs of the underlying pad remain undisturbed and in place securely holding the underlying pad in the desired position.

Figure 1A:
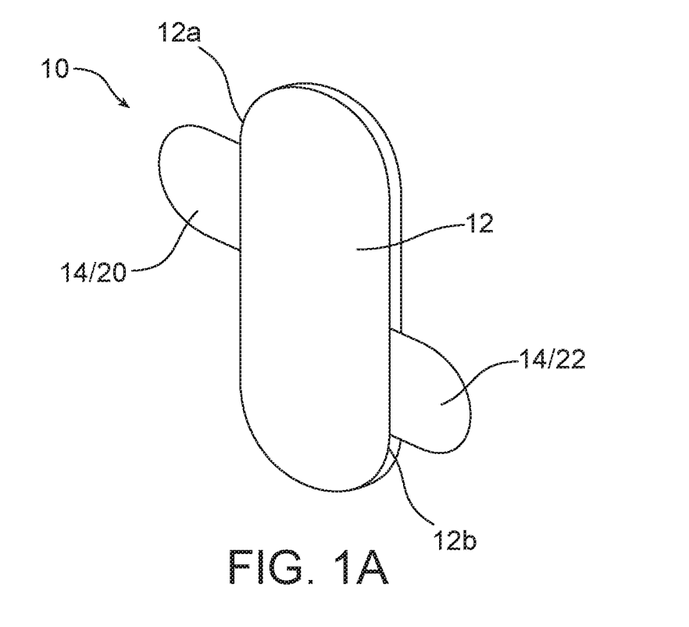
FIGS. 1A-1F illustrate a first embodiment of the sanitary pad system.
Figure 1B:
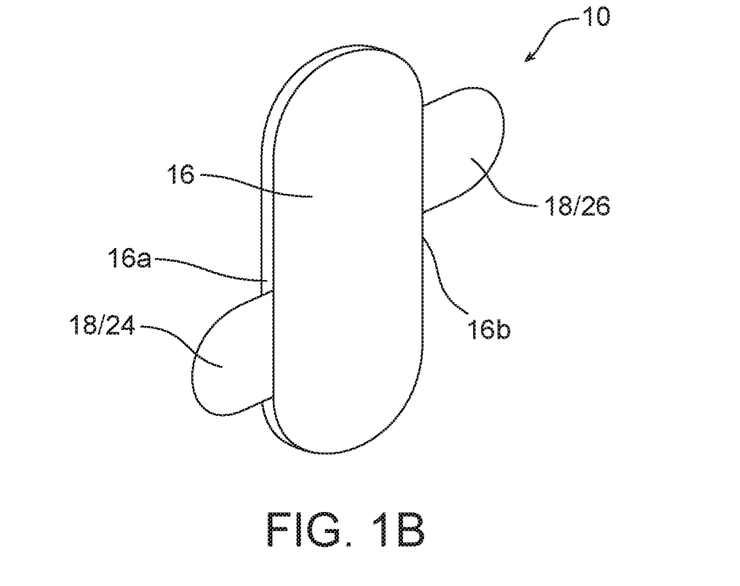

As used herein, the term "offset" signifies tabs which are non-overlapping, asymmetrical, or emanate from different areas of the pad edges on either side of the pad (e.g., such that they are not directly across from each other), or any combination thereof. For instance, in the present invention, FIG. 1A depicts tabs that are offset from each other in that they do not overlap and a first tab 14/20 emanates from the upper left edge of the pad while a second tab 14/22 emanates from a bottom right edge of the pad. The term "offset" can also be used herein to describe the tabs disposed in a sanitary pad system where there is no overlap of any of the tabs of a first pad and a second pad as shown and described relative to FIGS. 1C, 1D, 2A, and 2B.

Reference is now made to FIGS. 1A-1E illustrating a first possible embodiment of a sanitary pad system 10. That sanitary pad system 10 includes a first pad 12 including a first set of fastening tabs 14 adapted for attaching the first pad to an undergarment U of the wearer (see FIG. 1A). The sanitary pad system 10 further includes a second pad 16 having a second set of fastening tabs 18 for attaching the second pad to the undergarment U of the wearer (see FIG. 1B). More specifically, the second set of fastening tabs 18 are offset from the first set of fastening tabs 14 so that both pads 12, 16 may be directly attached to the undergarment U of the wearer when the second pad is stacked upon or overlies the first pad (see FIGS. 1C-1E).

More specifically, the first set of fastening tabs 14 includes two opposed and offset fastening tabs 20, 22 with a first fastening tab 20 of the first set of fastening tabs projecting from one edge 12a of the first pad 12 and a second fastening tab 22 of the first set of fastening tabs projecting from a second, opposite edge 12b of the first pad (see FIG. 1A). As shown, tabs 20 and 22 are not disposed across from each other; tab 20 emanates from the upper left edge portion of the pad 12 and tab 22 emanates from the lower right edge portion of the pad 12. The second set of fastening tabs 18 on the second pad 16 also includes two opposed and offset fastening tabs 24, 26 with a third fastening tab 24 of the second set of fastening tabs projecting from a corresponding first edge 16a of the second pad and a fourth fastening tab 26 of the second set of fastening tabs projecting from a corresponding second edge 16b of the second pad (see FIG. 1B). As shown, tabs 24 and 26 are not disposed across from each other; tab 24 emanates from the lower left edge portion of the pad 16 and tab 26 emanates from the lower right edge portion of the pad 16. Significantly, the third fastening tab 24 is also offset from the first fastening tab 20 and the fourth fastening tab 26 is also offset from the second fastening tab 22 when the first and second pads 12, 16 are in a stacked configuration.

Figure 1C:
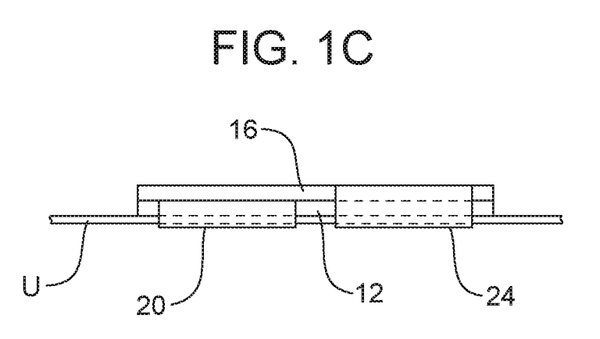
Figure 1D:
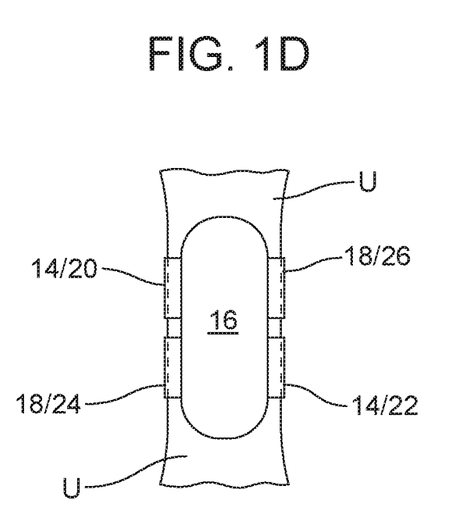
Figure 1E:
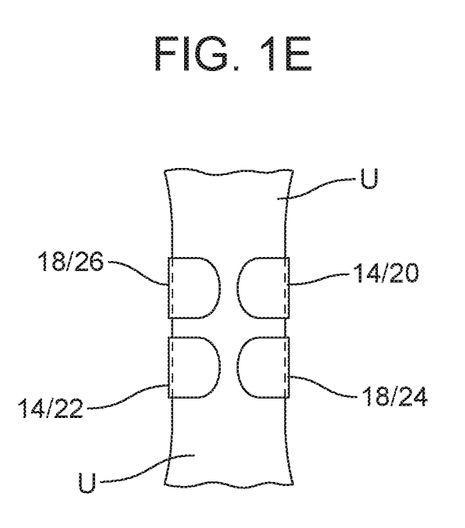
Figure 3:
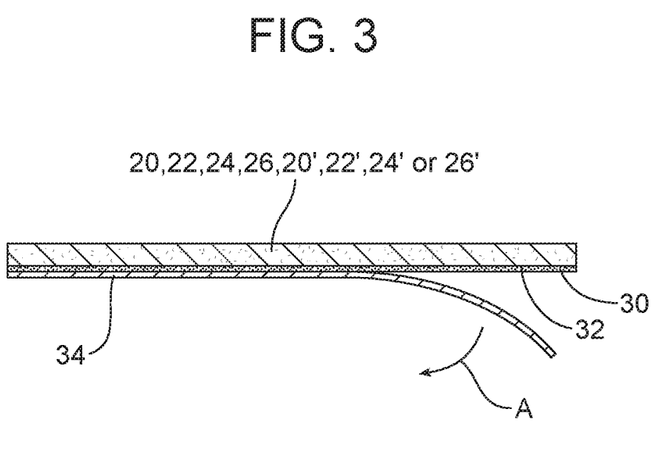
FIG. 3 is a cross sectional view of a fastening tab including a partially peeled release paper exposing an adhesive coating on a face of the fastening tab.

In use, the user attaches the first pad 12 to the undergarment at a desired position using the first set of fastening tabs 14. The user then positions the second pad 16 over the first pad and attaches the second pad to the undergarment U using the second set of fastening tabs 18. Here it should be appreciated that each fastening tab 20, 22, 24, 26 includes an adhesive surface (as shown in FIG. 3) for attaching the associated pad 12, 16 to an undergarment U of the wearer. The offset fastening tab arrangement is adapted to allow both pads 12, 16 to be adhered directly to an undergarment U of the wearer when the second pad 16 is stacked so as to overlie the first pad 12. A side view of the arrangement from the perspective of tab 14/20 and tab 18/24 of the first and second pads 12 and 16 respectively is shown in FIG. 1C. The present invention contemplates that tabs may each be of a different shape or size with respect to any other tab or that tabs 18 of the second pad may be of a different size or shape than the tabs 14 of the first pad. For instance, the tabs 18 of the second pad may be larger or longer than the tabs 14 of the first pad to accommodate the distance to the undergarment as shown in FIG. 1C.

Figure 1F:
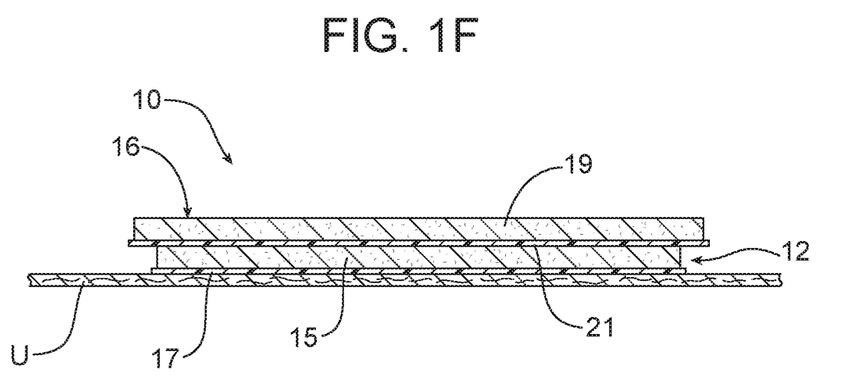

As illustrated in FIG. 1F, the first pad 12 may include an absorbent material layer 15 of a type known in the art, adapted to absorb body exudates such as menses and a liquid impervious backing layer 17. Similarly, the second pad 16 may include an absorbent material layer 19 and a liquid impervious backing layer 21. When stacked, the liquid impervious layer 21 of the second pad 16 prevents the body exudate being absorbed by the absorbent material layer 19 from soaking through and fouling the absorbent material layer 15 of the first pad 12. To further ensure this result, the second pad 16 may have a larger surface area than the first pad 12 so as to extend beyond the first pad over the entire perimeter thereof.

After a certain period of time, the second, overlying pad 16 has reached the end of its useful life. The user then removes the second pad 16 by releasing the second set of fastening tabs 18 from the undergarment U. As the second set of fastening tabs 18 is offset from the first set of fastening tabs 14 holding the first pad 12 in position on the undergarment U, the first pad remains secured in the desired position to absorb blood excreted from the vagina of the wearer. The user then disposes of the second pad 16.

More specifically, the liquid impervious backing layer 21 of the second pad 16 has a smooth, slick outer surface that will not stick to the underlying absorbent layer 15 of the first pad. Further, since the second fastening tab set 18 is offset from the first fastening tab set 14, the first fastening tab set is not subjected to any removal or releasing force and pulled free in any way when the second pad 16 is removed. Thus, the first pad 12 remains securely held in position on the undergarment U.

Once the useful life of the first pad 12 has expired, the first pad is subsequently removed by releasing the first set of fastening tabs 14. A new sanitary pad system 10 is then repositioned on the undergarment of the wearer if desired.

Figure 2A:
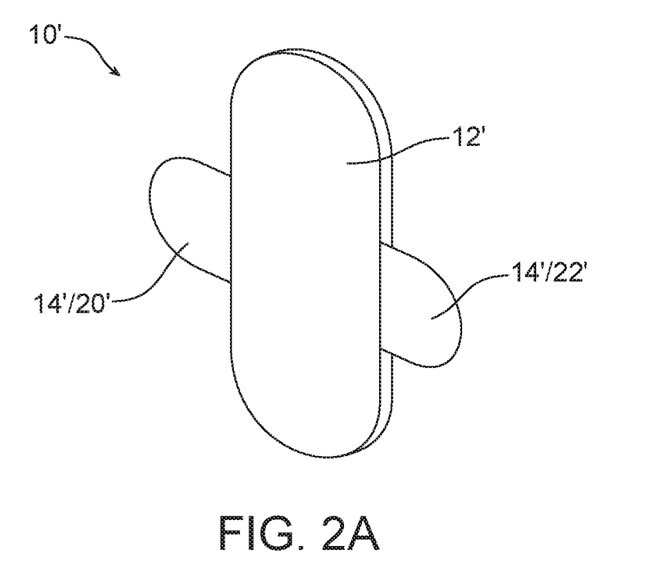
FIGS. 2A-2E illustrate a second embodiment of the sanitary pad system.
Figure 2B:
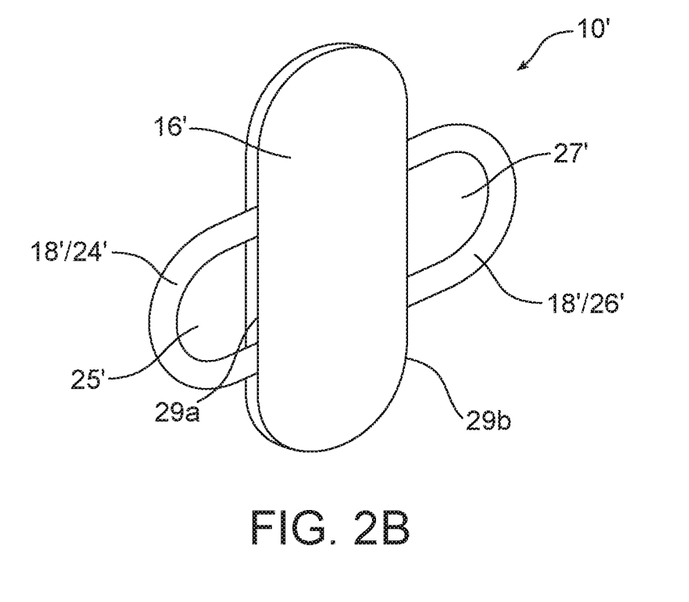
Figure 2C:
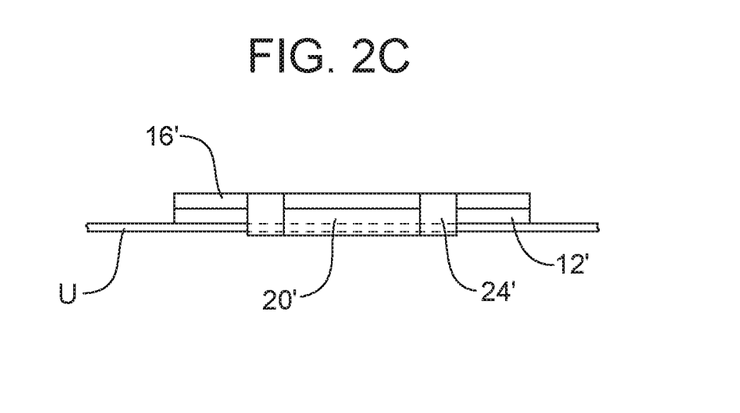
Figure 2D:
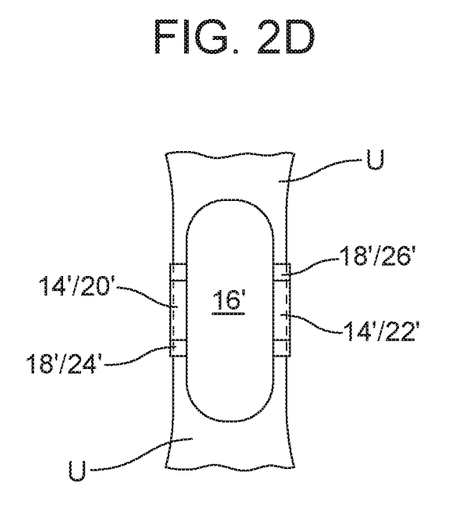
Figure 2E:
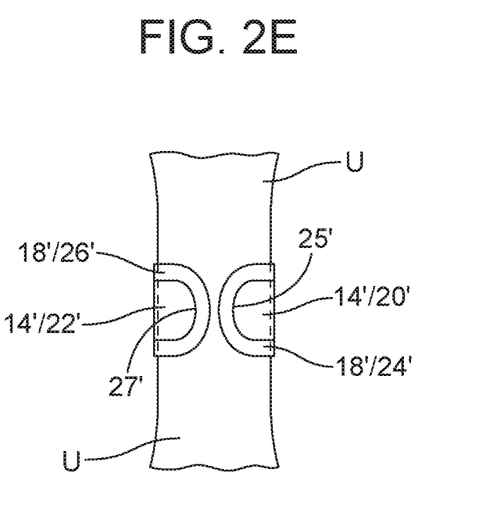

FIGS. 2A-2E illustrate an alternative embodiment of the sanitary pad system 10' very similar to the first embodiment illustrated in FIGS. 1A-1F except for the configuration of the two sets of offset fastening tabs 14', 18'. While the fastening tabs 20, 22, 24, 26 of the first and second set of fastening tabs 14, 18 in the first embodiment illustrated in FIGS. 1A-1F are all semi-circular in shape, the second set of fastening tabs 18' (including fastening tabs 24' and 26') in the second embodiment illustrated in FIGS. 2A-2E are substantially semi-annular in shape and adapted to extend around the first set of fastening tabs 14' (including fastening tabs 20' and 22') that are semi-circular in shape when the two pads 12', 16' are connected or adhered in an overlapping configuration to the undergarment U of the wearer. In other words, the first set of fastening tabs 14' fit within the semi-circular openings outlined by the second set of fastening tabs 18'. The tabs 14' and tabs 18' do not however, overlap. Note the first semi-circular opening 25a on receiver 25' formed between the tab 24' and the first edge 29a of the pad 16' and the second semi-circular opening 25b on receiver 27' formed between the tab 26' and the second edge 29b of the pad 16' as best illustrated in FIG. 2B. Receivers 25' and 27' of the present invention can comprise openings or apertures 25a and 25b of any feasible shape.

As should be appreciated, the fastening tab sets may assume other forms and shapes in addition to those illustrated in FIGS. 1A-1F and 2A-2E so long as the first and second set of fastening tabs 14, 18 are offset in a manner allowing the fastening tabs on both the first pad 12 and the second pad 16 to be adhered directly to the undergarment U of the wearer. Thus, for example, the first set of fastening tabs 14' could be semi-annular in shape while the second set of fastening tabs 18' could be semi-circular in shape: that is, the opposite of that illustrated in FIGS. 2A-2E. Alternatively, the fastening tabs 20, 22, 24, 26 could be a completely different shape than those illustrated such as rectangular or square.

As illustrated in FIG. 3, in any of the many possible embodiments, the fastening tab sets 14, 18, 14', 18' may comprise adhesive tabs including an adhesive coating 30 on one face 32. That adhesive coating 30 may be protected before use by a removable release paper 34. When one seeks to secure a pad 12, 16, 12', 16' to an undergarment U, one peels the release paper 34 from the tab 20, 22, 24, 26, 20', 22', 24', 26'. As this is done, the adhesive stays on the tab 20, 22, 24, 26, 20', 22', 24', 26' where it functions to adhere the tab to the undergarment U and thereby secure the associated pad 12, 16, 12', 16' in place.

The foregoing has been presented for purposes of illustration and description. It is not intended to be exhaustive or to limit the embodiments of the sanitary pad system 10, 10' to the precise form disclosed. Obvious modifications and variations are possible in light of the above teachings. For example, besides altering the number and shape of the fastening tabs, the pads 12, 16, 12', 16' may also have other adhesive surfaces. For example, the first pad 12, 12' could have an adhesive along its rear surface to adhere to the undergarment U. Further, while two stackable pads 12, 16, 12', 16' are shown in the illustrated embodiments, more than two could be provided. In addition, while disposable pads 12, 16, 12', 16' are contemplated, the pads could be washable and reusable if desired. All such modifications and variations are within the scope of the appended claims when interpreted in accordance with the breadth to which they are fairly, legally and equitably entitled.

What is claimed:

1. A sanitary pad system, comprising:
a first pad having a first set of fastening tabs; and
a second pad having a second set of fastening tabs wherein said second set of fastening tabs is offset from said first set of fastening tabs when said second pad is overlying said first pad whereby said first set of fastening tabs and said second set of fastening tabs are directly connected to an undergarment of a wearer.

2. The sanitary pad system of claim 1, wherein said first set of fastening tabs includes a first fastening tab projecting from a first edge of said first pad and a second fastening tab projecting from a second edge of said first pad.

3. The sanitary pad system of claim 2, wherein said first set of fastening tabs are semi-circular in shape.

4. The sanitary pad system of claim 2, wherein said first fastening tab is offset from said second fastening tab.

5. The sanitary pad system of claim 4, wherein said second set of fastening tabs includes a third fastening tab projecting from a first edge of said second pad and a fourth fastening tab projecting from a second edge of said second pad.

6. The sanitary pad system of claim 5, wherein said third fastening tab is offset from said fourth fastening tab.

7. The sanitary pad system of claim 6, wherein said first fastening tab, said second fastening tab, said third fastening tab and said fourth fastening tab are semi-circular in shape.

8. The sanitary pad system of claim 7, wherein the first fastening tab, the second fastening tab, the third fastening tab and the fourth fastening tab include an adhesive on one face thereof to adhere to the undergarment.

9. The sanitary pad system of claim 8, wherein the first fastening tab, the second fastening tab and the fourth fastening tab each include a removable release paper protecting the adhesive prior to use.

10. The sanitary pad system of claim 5, wherein said first fastening tab, said second fastening tab, said third fastening tab and said fourth fastening tab are each offset from each other.

11. The sanitary pad system of claim 10, wherein said second set of fastening tabs are semi-annular in shape.

12. The sanitary pad system of claim 11, wherein a first receiver is defined between the third fastening tab and the first edge of the second pad and a second receiver is defined between the fourth fastening tab and the second edge of the second pad.

13. The sanitary pad system of claim 12, wherein when said first pad and said second pad are connected to the undergarment in an overlapping configuration, the first fastening tab engages the undergarment at the first receiver and the second fastening tab engages the undergarment at the second receiver.

14. The sanitary pad system of claim 13, wherein the first fastening tab, the second fastening tab, the third fastening tab and the fourth fastening tab include an adhesive on one face thereof to adhere to the undergarment.

15. The sanitary pad system of claim 14, wherein the first fastening tab, the second fastening tab and the fourth fastening tab each include a removable release paper protecting the adhesive prior to use.

16. The sanitary pad system of claim 15, wherein the first pad and the second pad both include an absorbent material layer and a liquid impervious backing layer.

17. The sanitary pad system of claim 1, wherein the first pad and the second pad both include an absorbent material layer and a liquid impervious backing layer.

18. The sanitary pad system as set forth in claim 1, wherein the second set of fastening tabs are offset from the first set of fastening tabs so as to avoid overlap of the second set of fastening tabs with the first set of fastening tabs when the first pad and the second pad are directly connected to the undergarment.

* * * * *